(12) United States Patent
Plumptre

(10) Patent No.: US 10,369,291 B2
(45) Date of Patent: Aug. 6, 2019

(54) MECHANISM FOR A DRUG DELIVERY DEVICE

(71) Applicant: Sanofi-Aventis Deutschland GmbH, Frankfurt am Main (DE)

(72) Inventor: David Aubrey Plumptre, Worcestershire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 496 days.

(21) Appl. No.: 14/891,203

(22) PCT Filed: May 8, 2014

(86) PCT No.: PCT/EP2014/059405
§ 371 (c)(1),
(2) Date: Nov. 13, 2015

(87) PCT Pub. No.: WO2014/184081
PCT Pub. Date: Nov. 20, 2014

(65) Prior Publication Data
US 2016/0106926 A1    Apr. 21, 2016

(30) Foreign Application Priority Data

May 16, 2013 (EP) ..................................... 13167987

(51) Int. Cl.
*A61M 5/315*     (2006.01)
*A61M 5/24*      (2006.01)
(Continued)

(52) U.S. Cl.
CPC .......... *A61M 5/31515* (2013.01); *A61M 5/24* (2013.01); *A61M 5/31541* (2013.01);
(Continued)

(58) Field of Classification Search
CPC ............ A61M 5/31515; A61M 5/5086; A61M 5/31555; A61M 5/31541; A61M 5/31551;
(Continued)

(56) References Cited

U.S. PATENT DOCUMENTS

| 533,575 A | 2/1895 | Wilkens |
| 4,865,591 A | 9/1989 | Sams |

(Continued)

FOREIGN PATENT DOCUMENTS

| CA | 2138528 | 12/1998 |
| CA | 2359375 A1 | 7/2000 |

(Continued)

OTHER PUBLICATIONS

The Free Dictionary definition of resolution of a force available online Jan. 17, 2018 at https://www.thefreedictionary.com/Resolution+of+a+force.*

(Continued)

*Primary Examiner* — Amber R Stiles
(74) *Attorney, Agent, or Firm* — Fish & Richardson P.C.

(57) ABSTRACT

The present invention concerns a mechanism for a drug delivery device, having a longitudinal axis and comprising a first member comprising a first contact surface and a second member comprising a second contact surface, wherein the first member is configured to be assembled to the second member, wherein the first member and the second member are configured such that the first contact surface abuts the second contact surface when the first member is assembled to the second member, wherein the first contact surface is arranged such that a force applied to the mechanism in a direction parallel to the longitudinal axis is split up into a first component in a direction perpendicular to a surface normal of the first contact surface and a second component parallel to the surface normal, wherein the first (Continued)

member and the second member are configured such that the first member is detached from the second member by the force applied to the mechanism in a direction parallel to the longitudinal axis if the absolute value of the force is stronger than a first predetermined value, and wherein the first predetermined value is defined as the absolute value of the force which has a first component strong enough to move the first contact surface out of abutment with the second member.

14 Claims, 3 Drawing Sheets

(51) Int. Cl.
    *A61M 5/50*         (2006.01)
    *A61M 5/31*         (2006.01)

(52) U.S. Cl.
    CPC .... *A61M 5/31551* (2013.01); *A61M 5/31555* (2013.01); *A61M 5/31585* (2013.01); *A61M 5/5086* (2013.01); *A61M 2005/2407* (2013.01); *A61M 2005/3142* (2013.01)

(58) Field of Classification Search
    CPC ................ A61M 5/31585; A61M 5/24; A61M 2005/2407; A61M 2005/3142
    See application file for complete search history.

(56) References Cited

U.S. PATENT DOCUMENTS

| | | | |
|---|---|---|---|
| 5,092,842 A | | 3/1992 | Bechtold et al. |
| 5,226,895 A | | 7/1993 | Harris |
| 5,226,896 A | | 7/1993 | Harris |
| 5,279,586 A | | 1/1994 | Balkwill |
| 5,304,152 A | | 4/1994 | Sams |
| 5,320,609 A | | 6/1994 | Haber et al. |
| 5,378,233 A | | 1/1995 | Haber et al. |
| 5,383,865 A | | 1/1995 | Michel |
| 5,391,157 A | | 2/1995 | Harris et al. |
| 5,480,387 A | | 1/1996 | Gabriel et al. |
| 5,505,704 A | | 4/1996 | Pawelka et al. |
| 5,582,598 A | | 12/1996 | Chanoch |
| 5,626,566 A | | 5/1997 | Petersen et al. |
| 5,674,204 A | | 10/1997 | Chanoch |
| 5,688,251 A | | 11/1997 | Chanoch |
| 5,807,346 A | | 9/1998 | Frezza |
| 5,820,602 A | | 10/1998 | Kovelman et al. |
| 5,851,079 A | | 12/1998 | Horstman et al. |
| 5,921,966 A | | 7/1999 | Bendek et al. |
| 5,957,896 A | | 9/1999 | Bendek et al. |
| 5,961,495 A | | 10/1999 | Walters et al. |
| 6,004,297 A | | 12/1999 | Steenfeldt-Jensen et al. |
| 6,033,387 A | * | 3/2000 | Brunel .................. A61M 5/24 604/110 |
| 6,193,698 B1 | | 2/2001 | Kirchhofer et al. |
| 6,221,046 B1 | | 4/2001 | Burroughs et al. |
| 6,235,004 B1 | | 5/2001 | Steenfeldt-Jensen et al. |
| 6,248,095 B1 | | 6/2001 | Giambattista et al. |
| 6,562,006 B1 | | 5/2003 | Hjertman et al. |
| 6,613,023 B2 | | 9/2003 | Kirchhofer et al. |
| 6,699,224 B2 | | 3/2004 | Kirchhofer et al. |
| 6,899,698 B2 | | 5/2005 | Sams |
| 6,932,794 B2 | | 8/2005 | Giambattista et al. |
| 6,936,032 B1 | | 8/2005 | Bush, Jr. et al. |
| 7,169,132 B2 | | 1/2007 | Bendek et al. |
| 7,241,278 B2 | | 7/2007 | Moller |
| 7,678,084 B2 | | 3/2010 | Judson et al. |
| 7,850,662 B2 | | 12/2010 | Veasey et al. |
| 8,186,233 B2 | | 5/2012 | Joung et al. |
| 2002/0022807 A1 | * | 2/2002 | Duchon ............ A61M 5/14216 604/228 |
| 2002/0052578 A1 | | 5/2002 | Moller |
| 2002/0120235 A1 | | 8/2002 | Enggaard |
| 2003/0050609 A1 | | 3/2003 | Sams |
| 2004/0059299 A1 | | 3/2004 | Moller |
| 2004/0097883 A1 | | 5/2004 | Roe |
| 2004/0210199 A1 | | 10/2004 | Atterbury et al. |
| 2004/0267207 A1 | | 12/2004 | Veasey et al. |
| 2005/0096597 A1 | * | 5/2005 | Crawford ............ A61M 5/326 604/198 |
| 2005/0113765 A1 | | 5/2005 | Veasey et al. |
| 2006/0153693 A1 | | 7/2006 | Fiechter et al. |
| 2007/0016143 A1 | | 1/2007 | Miller et al. |
| 2009/0275916 A1 | | 11/2009 | Harms et al. |

FOREIGN PATENT DOCUMENTS

| | | | | |
|---|---|---|---|---|
| CN | | 1390145 | | 1/2003 |
| EP | | 0441628 A2 | | 8/1991 |
| EP | | 0496141 A1 | | 7/1992 |
| EP | | 0897729 A2 | | 2/1999 |
| EP | | 0937471 A2 | | 8/1999 |
| EP | | 0937476 A2 | | 8/1999 |
| EP | | 1776975 A2 | | 4/2007 |
| JP | | 2000/342683 | | 12/2000 |
| RU | | 2401134 | | 3/2009 |
| WO | | 9307322 A1 | | 4/1993 |
| WO | | 9324160 A1 | | 12/1993 |
| WO | | 0938554 A1 | | 8/1999 |
| WO | | 0110484 A1 | | 2/2001 |
| WO | WO 2001/030425 | | | 5/2001 |
| WO | | 0230495 A2 | | 4/2002 |
| WO | | 02092153 A2 | | 11/2002 |
| WO | | 03080160 A1 | | 10/2003 |
| WO | | 2004078239 A1 | | 9/2004 |
| WO | | 2006084876 A1 | | 8/2006 |
| WO | WO 2006/079481 | | | 8/2006 |
| WO | WO 2008/097338 | | | 8/2008 |
| WO | | 2012041931 A1 | | 4/2012 |
| WO | WO-2012041931 A1 | * | 4/2012 | ............ A61M 5/24 |
| WO | WO 2012041931 A1 | * | 4/2012 | ............ A61M 5/24 |

OTHER PUBLICATIONS

Chapter 2 of Engineering Mechanics: Statics, Chapter 2: Forces, pp. 23-50 available online in a Google Book search, available online Jan. 17, 2018 at https://books.google.com/books?id=pe_QRJ6wOtEC&pg=PA23&dq=resolution+of+forces&hl=en&sa=X&ved=0ahUKEwji7oqtguDYAhWIUd8KHR0LBygQ6AEIJjAA#v=onepage&q=resolution%20of%20forces&f=false.*
Free Dictionary definition of resolution of a force, available online Sep. 2, 2018 at https://www.thefreedictionary.com/Resolution+of+a+force.*
JJong, I.C, et al.; Engineering Mechanics: Statics, Chapter 2: Forces; pp. 23-50, avaialbe online Sep. 2, 2018 at https://books.google.com/books?id=pe_QRJ6wOtEC&pg=PA23&dq=resolution+of+forces&hl=en&sa=X&ved=0ahUKEwji7oqtguDYAhWIUd8KHR0LBygQ6AEIJjAA#v=onepage&q=resolution%20of%20forces&f=false.*
"Pen-injectors for medical use—Part 1: Pen-injectors—Requirements and test methods," International Standard, reference No. ISO 11608-1:2000(E), first edition Dec. 15, 2000, 32 pages.
International Search Report and Written Opinion in International Application No. PCT/EP2014/059405, dated Jun. 25, 2014, 11 pages.
International Preliminary Report on Patentability in International Application No. PCT/EP2014/059405, dated Nov. 17, 2015, 9 pages.

* cited by examiner

MECHANISM FOR A DRUG DELIVERY DEVICE

CROSS REFERENCE TO RELATED APPLICATIONS

The present application is a U.S. National Phase application pursuant to 35 U.S.C. § 371 of International Application No. PCT/EP2014/059405 filed May 8, 2014, which claims priority to European Patent Application No. 13167987.0 filed May 16, 2013. The entire disclosure contents of these applications are herewith incorporated by reference into the present application.

FIELD OF INVENTION

The present invention relates to a mechanism for a drug delivery device and to a drug delivery device incorporating such a mechanism. The mechanism may be e.g. a drive mechanism.

BACKGROUND

In certain situations, it may be desirable for a drug delivery device that a particular component interface fails under user generated abuse loading, in preference to another component interface.

Moreover, a mechanism for a drug delivery device should be designed such that it prevents the user from misusing the device, e.g. by applying excessive force, and that it warns the user from using a damaged mechanism.

SUMMARY

It is an object to provide for a mechanism for a drug delivery device which is constructed to ensure that problems are avoided when an excessive force is applied to the mechanism.

This object may be achieved by a mechanism according to claim 1. Further features, advantages and expedience are subject-matter of the dependent claims.

According to one aspect, a mechanism for a drug delivery device is provided wherein the mechanism has a longitudinal axis, wherein the mechanism comprises a first member comprising a first contact surface, wherein the mechanism comprises a second member, wherein the first member is configured to be assembled to the second member, wherein the first member and the second member are configured such that the first contact surface abuts the second member when the first member is assembled to the second member, wherein the first contact surface is arranged such that a force applied to the mechanism in a direction parallel to the longitudinal axis is split up into a first component in a direction perpendicular to a surface normal of the first contact surface and a second component parallel to the surface normal, wherein the first member and the second member are configured such that the first member is detached from the second member by the force applied to the mechanism in a direction parallel to the longitudinal axis if the absolute value of the force is stronger than a first predetermined value, and wherein the first predetermined value is defined as the absolute value of the force which has a first component strong enough to move the first contact surface out of abutment with the second member.

The mechanism may be a drive mechanism. Accordingly, the mechanism may be used to carry out a dose delivery operation. A dose delivery operation is an operation that is activated by a user, wherein during the operation, the drive mechanism may deliver a dose of a drug out of the drug delivery device.

The mechanism may also be a dose setting mechanism. A dose setting mechanism may be used to carry out a dose setting operation. A dose setting operation is also activated by a user before dispensing a dose. During the dose setting operation, the drive mechanism is prepared to deliver a dose of a drug. For example, the drive mechanism may be brought into a state such that the user only needs to press a button to deliver a dose.

Moreover, the drug delivery device may be an injection device. The drug delivery device may be a pen-type device, in particular a pen-type injector. The device may be a disposable or a re-usable device. The device may be configured to dispense variable, preferably user-settable, doses of the drug. Alternatively, the device may be a fixed-dose device, in particular a device configured to dispense doses of the drug which may not be varied by the user. The drug delivery device may be a manually, in particular a non-electrically, driven device.

In particular, the drug delivery device may be a device as described in WO 2004/078239 A1, the content of which is hereby incorporated by reference.

The longitudinal axis of the mechanism may be a symmetry axis. The longitudinal axis of the mechanism may extend from a distal end of the mechanism to a proximal end of the mechanism. The term "distal end" designates that end of the mechanism which is to be arranged closest to a dispensing end of the drug delivery device when the mechanism is assembled into the drug delivery device. The term "proximal end" designates that end of the mechanism which is to be arranged furthest away from the dispensing end of the device.

Further, the longitudinal axis of the mechanism may be parallel to a longitudinal axis of the drug delivery device. The longitudinal axis of the drug delivery device may extend from a distal end of the device to a proximal end of the device.

The first and the second member of the mechanism may be members that are engaged with each other during an assembly of the mechanism. However, once the first and the second member are engaged to each other, they may be constructed such that they are not movable relative to each other during a normal operation of the device. Hereby, the term "normal operation" is understood as an operation wherein non-excessive forces are applied to the mechanism. In particular, during the normal operation of the mechanism, only axial forces having a strength below the first predetermined value are applied to the mechanism. The term "axial force" designates a force that is applied to the mechanism in a direction parallel to the longitudinal axis of the mechanism.

In particular, one of the first member and the second member may be a dial grip of the mechanism. Accordingly, said one of the first member and the second member may be gripped directly by the user. The one of the first member and the second member may be operated, in particular rotated, during a dose setting operation of the mechanism. As the first member may be fixed to the second member during the normal operation of the device, the other one of the first and the second member may be constructed such that it follows a rotation of the one of the first and the second member. The other one of the first and the second member may be a dose dial sleeve. The other one of the first and the second member may be rotated during a dose setting operation.

Each of the first and second member may comprise a contact surface. The angle formed between the surface normal of the first contact surface of the first member and the longitudinal axis of the device may define the first predetermined value of the axial force that needs to be applied to detach the first and the second member from each other. Accordingly, the angle formed between the surface normal of the first contact surface and the longitudinal axis may be chosen such that it is ensured that the first and the second member are the first member pair of the mechanism that is detached from each other.

Thus, the first and the second member may be considered as a security device. As the first and the second member may be the first member pair that is detached from each other they ensure that no other member pair is damaged by an excessive axial force. In particular, they may ensure that no internal member pair is damaged by an excessive axial force.

If the mechanism is modified by adjusting the angle between the surface normal of the first contact surface and the longitudinal axis, the first predetermined value can be amended. Accordingly, the angle may be chosen such that a desired detachment force is provided. However, the force required to detach the first member from the second member may further depend from other parameters, e.g. the coefficient of friction of the surface material of the first and the second member. Said other parameters may have to be considered as well when determining the first predetermined value.

When the first and the second member are detached from each other by an axial force stronger than the first predetermined value, it may become obvious to the user that the mechanism is not operable any more. The first and the second member may be constructed such that they cannot be reassembled to each other by the user. In particular, the first and the second member may only be reassembled by the use of special tools not available to the user. Thereby, the user is warned that the device is damaged and that the device may no longer be used.

The contact surface of the first member may also be arranged such that the surface normal of the first contact surface and the longitudinal axis are parallel to each other.

The mechanism is configured such that the surface normal of the first contact surface and the longitudinal axis may form an angle when the first member is assembled to the second member. Thereby, it is ensured that the first member may be detached from the second member if a sufficiently strong axial force is applied, i.e. if an axial force stronger than the first predetermined value is applied. In this case, the first member may slide along the second member.

It is possible to tune the angle such that a desired splitting of the force into the first component perpendicular to the surface normal and the second component parallel to the surface normal is realized. Thereby, the mechanism can be configured such that a desired first predetermined value is realized.

The angle may be an acute angle. When the angle is acute, it is possible to use a first member and a second member of a great variety of materials. In particular, no strict restrictions regarding the stiffness of the material of the first and the second member occur.

However, the angle may also be an obtuse angle. Further, the surface normal of the first contact surface and the longitudinal axis may also be parallel. In said last two cases, the first engagement feature has to be sufficiently stiff to allow for a disengagement of the first and the second member in case an axial force of sufficient strength is applied to the mechanism.

Furthermore, the contact surface of the second member may be arranged such that the surface normal of the contact surface of the second member and the longitudinal axis of the device form a defined angle. This defined angle may also influence the predetermined value of the axial force that needs to be applied to detach the first and the second member from each other. Preferably, the first and the second member may be configured such that the contact surface of the second member and the contact surface of the first member are arranged parallel to each other when the first and the second member are engaged with each other.

The first and the second member may be constructed such that only the first component of the force contributes to detaching the first member from the second member. Due to the arrangement of the first contact surface, the second component may not contribute to detaching the first member from the second member.

The first member and the second member may be configured such that the first member is axially and rotationally locked to the second member when the first member is assembled to the second member. Accordingly, the first member may not be movable relative to the second member during normal operation of the device.

The first member may comprise a first engagement feature and the second member may comprise a second engagement feature configured to be engaged with the first engagement feature of the first member. The first engagement feature may comprise a biased element. The first engagement feature may be constructed such that the biased element is deformed during an engagement and during a disengagement of the first and the second member. In particular, the first and the second engagement feature may be configured to form a snap-fit engagement. The first predetermined value may be defined such that the first member is detached from the second member when an axial force is applied to the mechanism having a first component in a direction perpendicular to the surface normal of the first contact surface strong enough to deform the biased element.

Moreover, the second engagement feature may comprise a projection configured to deform the first engagement feature during an engagement of the first and the second member. Moreover, the projection may be configured to hold the first engagement feature in its position once the first and the second member are engaged with each other.

Furthermore, the mechanism may comprise a third and a fourth member, wherein the third member is configured to be assembled to the fourth member such that the third member is detached from the fourth member by the force applied to the mechanism in a direction parallel to the longitudinal axis if the absolute value of the force is stronger than a second predetermined value, and wherein the first predetermined value is smaller than the second predetermined value.

In particular, the third and the fourth member may be internal members of the mechanism. Thus, a detachment of the third and the fourth member from each other may not be easily noticeable for the user. Therefore, it is preferred that the first and the second member are detached from each other before the third and the fourth member are detached such that the user is warned of a damaging of the mechanism by the detachment of the first and the second member. In particular, a detachment of the third and the fourth member may result in a reduced dose accuracy of the mechanism.

At least one of the first member and the second member may be an external member of the mechanism. When one of the first and the second member is an external member, a detachment of the first and the second member is immediately visible to the user. In contrast to this, a detachment of two internal members, e.g. an insert and a body, may not be noticed by the user such that a user may not notice a failure of the mechanism. This may result in a user using a damaged mechanism which may lead to problems regarding the dispense accuracy of the mechanism.

Alternatively, the first and the second member may both be internal members wherein the mechanism is constructed such that an operation of the mechanism is prevented when said members are disengaged from each other. In this case, the user is warned regarding the damaged mechanism by not being able to operate the mechanism, thereby also preventing an operation of a damaged mechanism.

Further, the first and the second member may be constructed such that if they are detached from each other, this will not give the user access to the internal members of the mechanism.

In particular, one of the first and the second member may be configured to be gripped by a user during an operation of the mechanism.

Moreover, the mechanism may further comprise a fifth member which is mechanically engaged with one of the first member or the second member and which is configured such that the fifth member is damaged when the first member and the second member are detached from each other by the force applied to the mechanism in a direction parallel to the longitudinal axis having an absolute value stronger than the first predetermined value. In particular, the fifth member may be configured such that it is damaged in this case in a way that prevents a further operation of the mechanism, e.g. a dose setting operation and/or a dose delivery operation. In particular, the fifth member may be a button or a clutch. The fifth member may be an internal member or an external member.

According to a second aspect, a drug delivery device is provided comprising a mechanism as discussed above. The mechanism may be identical to the mechanism discussed above such that every structural and functional feature disclosed with respect to the mechanism may also be present regarding the drug delivery device.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa http://en.wikipedia.org/wiki/Dalton_%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Further features, refinements and expediences become apparent from the following descriptions of the exemplary embodiments in connection with the figures.

FIG. 1 shows a cross-sectional view of a drug delivery device 1. The drug delivery device 1 comprises a mechanism 2. The mechanism 2 is a drive mechanism.

DETAILED DESCRIPTION

Figure 1:
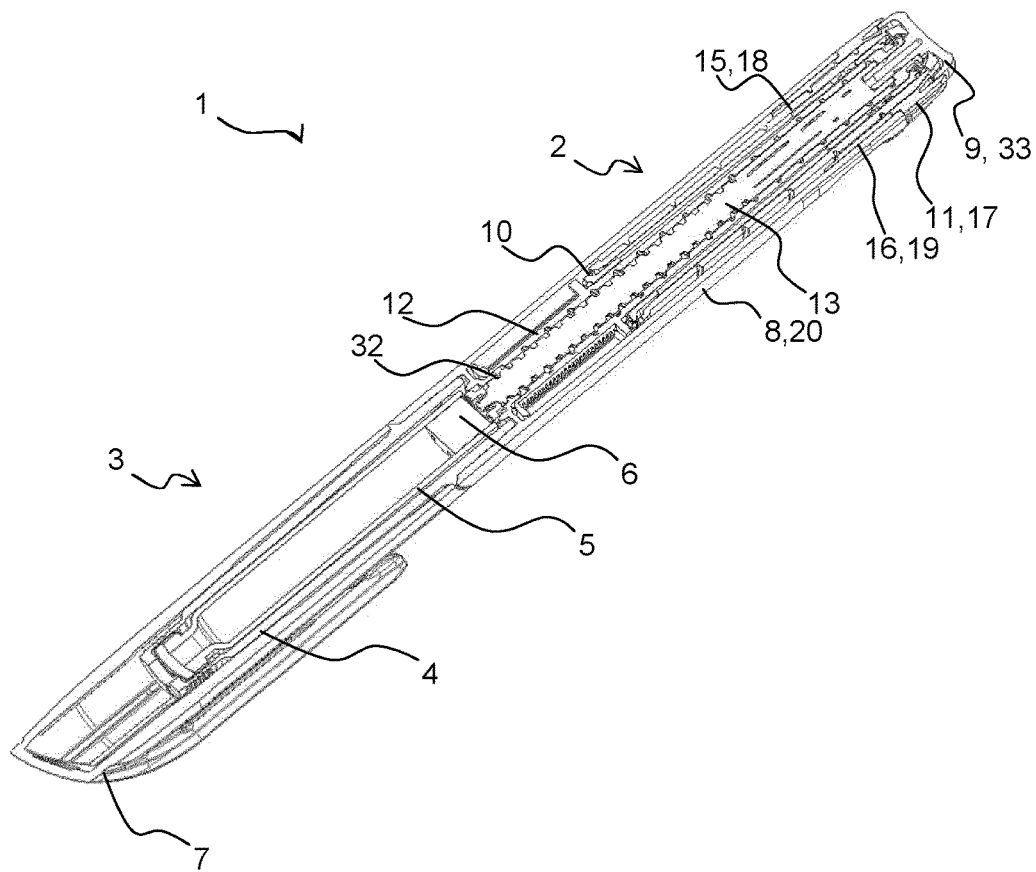
FIG. 1 shows a cross-sectional view of a drug delivery device.

The drug delivery device 1 further comprises a cartridge sub-assembly 3. The cartridge sub-assembly 3 comprises a cartridge holder 4 which is configured to comprise a cartridge 5. A number of doses of a drug may be dispensed from the cartridge 5. A piston 6 is retained in a proximal end of the cartridge 5.

A removable cap 7 is releasably retained over a distal end of the cartridge sub-assembly 3. In use, the removal cap 7 can be replaced by a user with a suitable needle unit (not shown).

Further, the mechanism 2 comprises a body 8, a button 9, a clutch 10, a dial grip 11, a drive sleeve 12, a piston rod 13, a dose dial sleeve 15 and an insert 16.

The cartridge sub-assembly 3 is secured to the body 8. The body 8 may be a housing of the drug delivery device 1. Further, the body 8 may comprise a threaded circular opening 32.

Further, the insert 16 is provided inside the body 8. The insert 16 is secured against rotational or longitudinal movement relative to the body 8. The insert 16 is provided with a threaded circular opening extending therethrough. The threaded circular opening is provided at a distal end of the insert 16.

The dose dial sleeve 15 is threadedly engaged with the threaded circular opening of the insert 16. The piston rod 13 is threadedly engaged with the threaded circular opening 32 of the body 8.

The dial grip 11 is an external member of the mechanism 2 such that it is easily operable for a user. The dial grip 11 is rotationally and axially locked to the dose dial sleeve 15.

To dial a dose, a user rotates the dial grip 11. Thereby, the dose dial sleeve 15, the drive sleeve 12 and the clutch 10 rotate together with the dial grip 11. The dose dial sleeve 15 and the drive sleeve 12 are moved in the proximal direction relative to the piston rod 13.

When a desired dose has been dialed, the user may dispense the dose by depressing the button 9. This displaces the clutch 10 axially with respect to the dose dial sleeve 15, thereby disengaging the clutch 10 from the dose dial sleeve 15.

By depressing the button 9, the drive sleeve 12 is moved axially in the distal direction. This causes the piston rod 13 to rotate through the threaded circular opening 32 in the body 8, thereby advancing the piston 6 in the cartridge in the distal direction.

Once the desired dose has been dispensed, the dose dial sleeve 15 is prevented from further rotating by a stop feature (not shown). Further, the clutch 10 and the dose dial sleeve 15 are reengaged.

Moreover, the mechanism 2 comprises a last dose nut (not shown) configured to prevent a dose setting after a certain number of doses has been set.

The discussion above refers to a normal operation by a user. However, it is possible that a user who is not familiar with the mechanism 2 operates the mechanism 2 in a way that is not anticipated. For example, the user may apply an abusive tensile force by pulling the dial grip 11 or other members of the mechanism 2 in the proximal direction with a large axial force.

In such a situation, it is desirable to ensure that certain component interface fails under the user-generated abuse loading before other component interfaces are damaged by the user-generated load. In the case of the drug delivery device 1 shown in FIG. 1, it is desirable that a first member 17 is detached from a second member 18 before a third member 19 is detached from a fourth member 20 when an axial load is applied excessively.

In the discussed embodiment, the first member 17 is the dial grip 11. Further, in this embodiment, the second member 18 is the dose dial sleeve 15. The third and the fourth member 19, 20 may be the threaded insert 16 and the body 8. However, in alternate embodiments, the first to fourth member 17-20 may be other elements of the mechanism 2. In principle, it is possible to design the mechanism 2 such that each member pair may be the first and the second member 17, 18 which are designed to be detached from each other first when a large axial force is applied.

In particular, the first and the second member 17, 18 are defined as the members that disengaged from each other first when an excessive axial load is applied to the mechanism 2. When one of the first and the second member 17, 18 is an external member, a detachment of the first and the second member 17, 18 is immediately visible to the user.

The first member 17 and the second member 18 are configured such that they are fixed to each other when the first member 17 is assembled to the second member 18. Thus, the first member 17 is locked axially and rotationally relative to the second member 18 when the first and the second member 17, 18 are assembled.

Moreover, one of the elements of the mechanism 2 is a fifth member 33 which is defined by being mechanically engaged with one of the first member 17 or the second member 18 and by being configured such that the fifth member 33 is damaged when the first member 17 and the second member 18 are detached from each other by the force applied to the mechanism 2 in a direction parallel to the longitudinal axis 21 having an absolute value stronger than the first predetermined value. In the embodiment shown in FIG. 1, the button 9 is the fifth member 33. Thus, when the first member 17 and the second member 18 are detached from each other by an excessive force, this results in a damage of the button 9, thereby preventing any further operation of the mechanism 2. The fifth member 33 may also be formed by any other element of the mechanism, e.g. by clutch 10.

Figure 2:
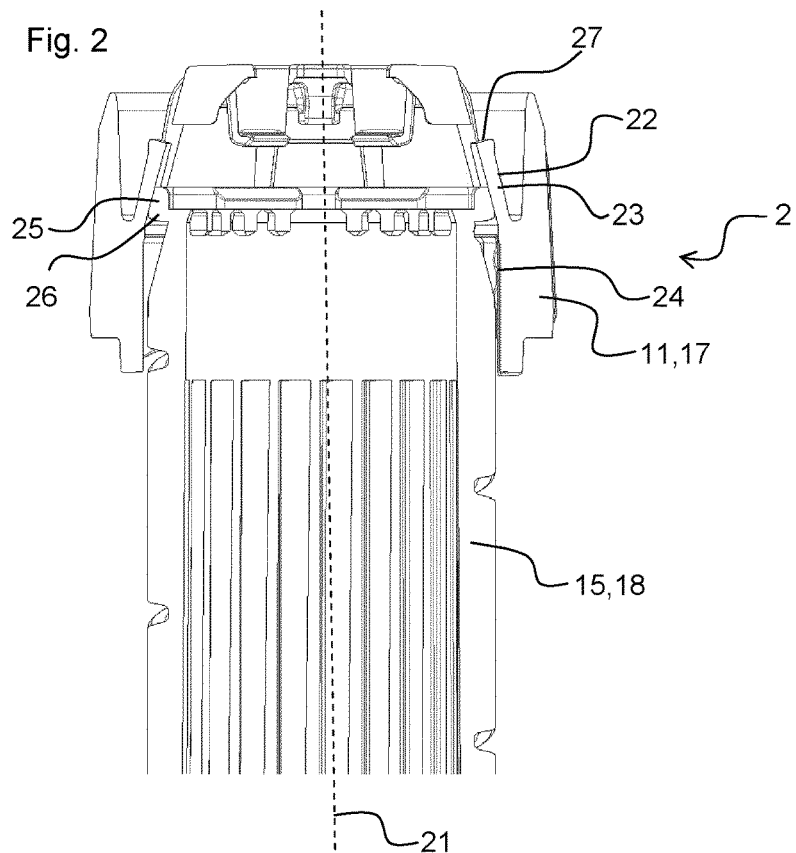
FIG. 2 shows a cross-sectional view through the mechanism during assembly wherein the first member is not assembled to a second member.

FIG. 2 shows a cross-sectional view of a part of the mechanism 2 during assembly before the first member 17 is assembled to the second member 18.

The mechanism 2 has a longitudinal axis 21. The terms "inward" and "outward" are defined relative to the longitudinal axis 21. Accordingly, "inward" refers to a direction pointing towards the longitudinal axis 21 and "outward" refers to a direction pointing away from the longitudinal axis 21.

The first member 17 comprises a first engagement feature 22. The first engagement feature 22 comprises a biased element 23. The biased element 23 is arranged at an internal surface 24 of the first member 17. The biased element 23 protrudes inwards from the remainder of the first member 17.

The second member 18 comprises a second engagement feature 25. The second engagement feature 25 comprises a projection 26. The second engagement feature 25 protrudes outwardly from the remainder of the second member 18.

The first member 17 is assembled to the second member 18 by moving the first member 17 axially in the distal direction relative to the second member 18.

Figure 3:
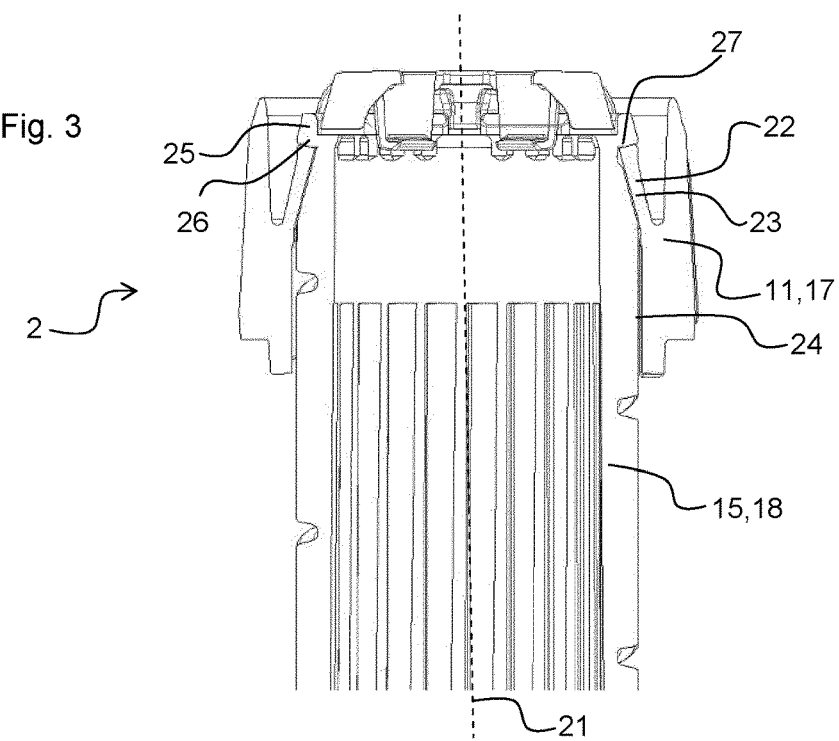
FIG. 3 shows a cross-sectional view through the mechanism shown in FIG. 2 wherein the first member is assembled to the second member.

FIG. 3 shows a cross-sectional view of a part of the mechanism 2 when the first member 17 is assembled to the second member 18. During the assembly, the first engagement feature 22 engages the second engagement feature 25. In particular, the first engagement feature 22 slides over the second engagement feature 25. Thereby, the second engagement feature 25 causes the biased element 23 to deform outwardly, i.e. away from the longitudinal axis 21 of the mechanism 2. When the first member 17 has moved axially far enough for the biased element 23 to pass over the second engagement feature 22, the biased element 23 deflects back to its original position. Accordingly, the first member 17 and the second member 18 are configured to be engaged with each other by a snap-fit engagement of the first and the second engagement feature 22, 25.

In particular, the biased element 23 of the first member 17 may comprise four retention arms. Further, the second engagement feature 22 of the second member 18 may comprise four flange features corresponding to the retention arms.

The engagement between the first member 17 and the second member 18 has a strength sufficient to survive any force generated during normal use of the mechanism 2. However, if a very large axial tensile force, which is far beyond what is expected during normal use, were applied to the first member 17, the first member 17 will be detached from the second member 18.

In particular, the mechanism 2 is constructed such that the first and the second member 17, 18 are detached from each other in this situation before any other member pair of the mechanism 2 is detached. Such other member pair is formed e.g. by the insert 16 and the body 8.

The first and the second member 17, 18 are constructed such that they are detached from each other when the axial force applied to the mechanism 2 exceeds a first predetermined value. Further, the other member pairs of the mechanism 2 are constructed such that they are not detached from each other when the axial force applied to the mechanism 2 reaches the first predetermined value. The other member pairs are constructed such that they are detached from each other only when the axial force applied to the mechanism 2 exceeds a second predetermined value which is higher than the first predetermined value. Thereby, it is ensured that the first member 17 will in any case be detached from the second member 18 before any other member pair is detached from each other.

Figure 4:
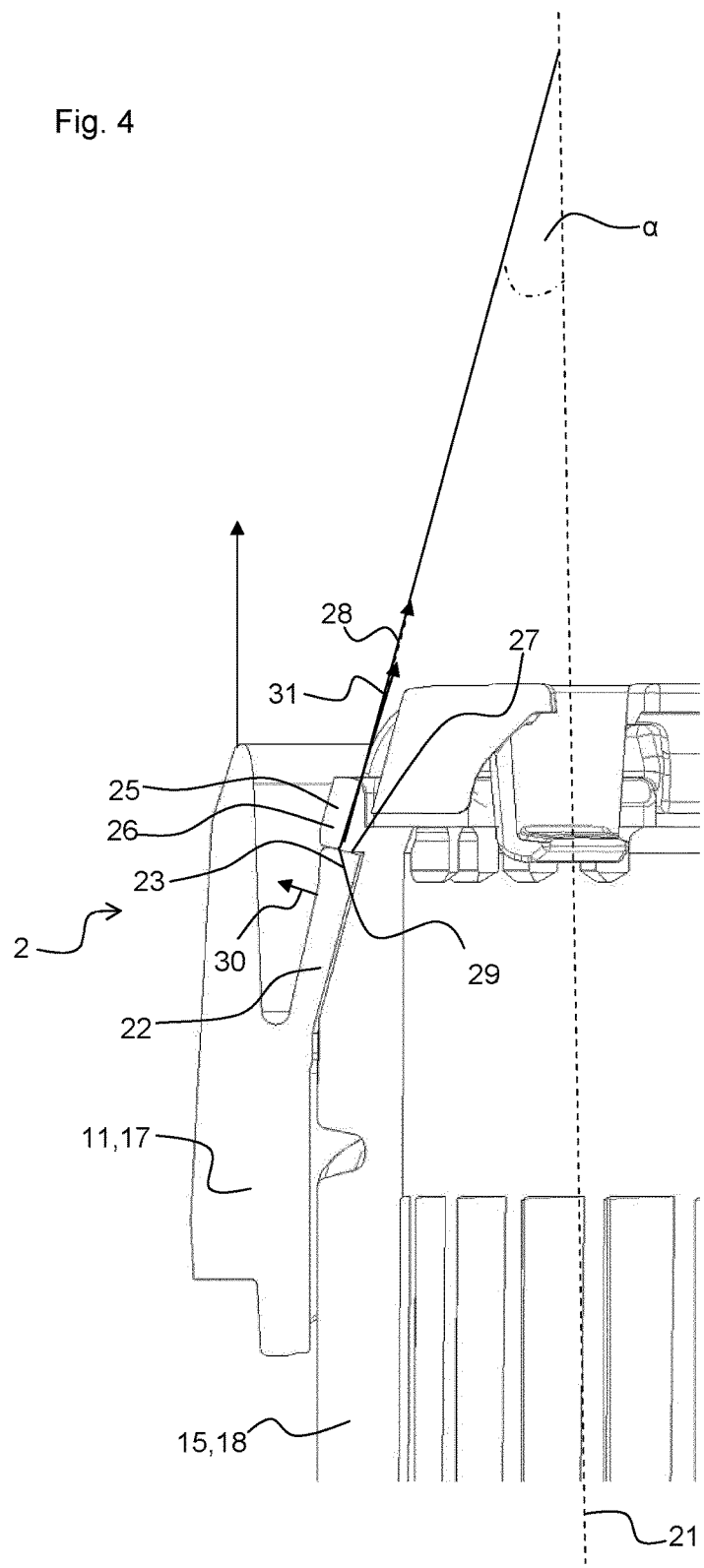
FIG. 4 shows a more detailed view of the engagement of the first and the second member.

FIG. 4 shows a more detailed view of an engagement of the first and the second member 17, 18.

The first member 17 comprises a first contact surface 27. In particular, the first contact surface 27 is a proximal facing surface of the biased element 23. The first contact surface 27 has a surface normal 28 which draws an angle $\alpha$ with the longitudinal axis 21 of the mechanism 2. The angle $\alpha$ may be acute, allowing an easier disengagement of the first and the second member 17, 18.

However, the angle $\alpha$ may also be an obtuse angle. Further, the surface normal 28 and the longitudinal axis 21 may also be parallel. In said last two cases, the first engagement feature 22 has to be sufficiently stiff to allow for a disengagement of the first and the second member 17, 18 in case an axial force of sufficient strength is applied to the mechanism 2.

Further, the second member 18 has a second contact surface 29. The first member 17 and the second member 18 are configured such that the first and the second contact surface 27, 29 abut each other when the first member 17 is attached to the second member 18. The second contact surface 29 is a distally facing surface of the second engagement feature 25. The second contact surface 29 is parallel to the first contact surface 27 when the first member 17 is attached to the second member 18.

When an axial force is applied to the mechanism 2 by a user, the user can apply this force only to an external member of the mechanism 2. The first member 17 is an external member of the mechanism 2. Thus, the axial force may be applied directly to the first member 17 by the user.

The axial force applied to the mechanism 2 is split up into a first component 30 and a second component 31. The first component 30 is perpendicular to the surface normal 28 of the first contact surface 27. The second component 31 of the axial force is parallel to the surface normal 28 of the first contact surface 27. The first member 17 and the second member 18 are constructed such that the second component 31 is not relevant for disengaging the first and the second member 17, 18. When the first component 30 is large enough, i.e. large enough to deform the biased element 23, the biased element 23 is deformed inwardly such that it slides along the second contact surface 29. Thereby, the first member 17 is disengaged from the second member 18. Accordingly, the first predetermined value is defined such that the first member 17 is disengaged from the second member 18 when the first component 30 of the axial force is large enough to deform the biased element 23.

The angle α between the longitudinal axis 21 of the mechanism 2 and the surface normal 28 of the first contact surface 27 thereby determines the first predetermined value. When the angle α decreases, the first component 30 decreases as well such that the first predetermined value is increased. Vice versa, if the angle α increases, the first predetermined value is decreased. Therefore, the angle α can be varied from one mechanism 2 to another to optimize the failure load so that the correct sequence of failure occurs.

The invention claimed is:

1. A mechanism for a drug delivery device, wherein the mechanism has a longitudinal axis, the mechanism comprising:
a first member, a second member, and an additional member that is mechanically engaged with the first member or the second member, the first member comprising a first contact surface and
the first member being configured to be assembled to the second member,
wherein the first member and the second member are configured such that the first contact surface abuts the second member when the first member is assembled to the second member,
wherein the first contact surface is arranged such that a force applied to the mechanism in a direction parallel to the longitudinal axis is split up into a first component in a direction perpendicular to a surface normal of the first contact surface and a second component parallel to the surface normal,
wherein the first member and the second member are configured such that the first member is detachable from the second member by the force applied to the mechanism in a direction parallel to the longitudinal axis if an absolute value of the force is greater than a first predetermined value,
wherein the first predetermined value is defined as the absolute value of the force which has a first component sufficient to move the first contact surface out of abutment with the second member, and
wherein the additional member is configured such that the additional member is damaged when the first member and the second member are detached from each other by the force applied to the mechanism in the direction parallel to the longitudinal axis having an absolute value greater than the first predetermined value thereby preventing any further operation of the mechanism.

2. The mechanism according to claim 1,
wherein the mechanism is configured such that the surface normal of the first contact surface and the longitudinal axis form an angle (a) when the first member is assembled to the second member.

3. The mechanism according to claim 1,
wherein the first member and the second member are constructed such that only the first component of the force applied to the mechanism in the direction parallel to the longitudinal axis contributes to detaching the first member from the second member.

4. The mechanism according to claim 1,
wherein the first member and the second member are configured such that the first member is axially and rotationally locked to the second member when the first member is assembled to the second member.

5. The mechanism according claim 1,
wherein the first member comprises a first engagement feature and the second member comprises a second engagement feature configured to be engaged with the first engagement feature of the first member.

6. The mechanism according to claim 5,
wherein the first engagement feature comprises a biased element.

7. The mechanism according to claim 6,
wherein the first engagement feature is constructed such that the biased element is deformed during an engagement and during a disengagement of the first and second members.

8. The mechanism according to claim 6,
wherein the first predetermined value is defined as the absolute value of the force which has a first component sufficient to deform the biased element, thereby moving the first contact surface out of abutment with the second member.

9. The mechanism according to claim 5,
wherein the second engagement feature comprises a projection configured to deform the first engagement feature during an engagement of the first and second members.

10. The mechanism according to claim 1,
wherein the second member comprises a second contact surface which is parallel to the first contact surface when the first member is engaged with the second member.

11. The mechanism according to claim 1,
further comprising a third member and a fourth member,
wherein the third member is configured to be assembled to the fourth member such that the third member is detachable from the fourth member by the force applied to the mechanism in the direction parallel to the longitudinal axis if the absolute value of the force is greater than a second predetermined value,
wherein the first predetermined value is smaller than the second predetermined value.

12. The mechanism according to claim 1,
wherein at least one of the first member and the second member is an external member.

13. The mechanism according to claim 1,
wherein one of the first member and the second member is configured to be gripped by a user operating the mechanism.

14. A drug delivery device comprising a mechanism according to claim 1.

* * * * *

UNITED STATES PATENT AND TRADEMARK OFFICE
CERTIFICATE OF CORRECTION

PATENT NO.         : 10,369,291 B2
APPLICATION NO.    : 14/891203
DATED              : August 6, 2019
INVENTOR(S)        : David Aubrey Plumptre It is certified that error appears in the above-identified patent and that said Letters Patent is hereby corrected as shown below:

In the Claims

Column 14, Line 8, Claim 5, after "according", insert -- to --.

Signed and Sealed this
Third Day of December, 2019

Andrei Iancu
*Director of the United States Patent and Trademark Office*